United States Patent [19]

Sprague

[11] Patent Number: Plant 6,119

[45] Date of Patent: Mar. 1, 1988

[54] *PRUNUS PERSICA* LAST CHANCE PEACH NUMBER ONE

[76] Inventor: James W. Sprague, 23500 West Ave., D-15, Lancaster, Calif. 93534

[21] Appl. No.: 855,832

[22] Filed: Apr. 24, 1986

[51] Int. Cl.[4] ..... A01H 5/03

[52] U.S. Cl. ..... Plt./43

[58] Field of Search ..... Plt./43

*Primary Examiner*—Robert E. Bagwill

*Attorney, Agent, or Firm*—Lyon & Lyon

[57] ABSTRACT

A new and distinct variety of *Prunus persica* characterized by its leaf size and inflorescent and fruit ripening patterns, particularly adapted for the commercial production of peaches.

4 Drawing Figures

BACKGROUND

The present invention relates to a new and distinct variety of *Prunus persica*, the novel characteristics of which reside particularly in the small size of the leaf and the late inflorescent and fruit ripening patterns of the tree.

The new Prunus was first discovered by James W. Sprague in 1983. It originated from a sport branch on a *Prunus persica* tree of the Last Chance Peach Variety, growing in a cultivated orchard in the West Antelope Valley of Lancaster, Calif. Thereafter, the new variety was successfully asexually reproduced by Mr. Sprague by budding from the sport onto root stock of the Last Chance Peach variety. Such asexual reproduction resulted in several progeny trees which have consistently displayed the leaf size and inflorescent and fruit ripening patterns found on the parent sport branch.

An interesting characteristic of the new variety is its relatively small leaf size. The average mature leaf measures approximately four to four and one-half inches in length by one and one-half inches in width. Another interesting characteristic of the new variety is its seasonally late inflorescent and fruit ripening patterns. The new variety flowers during the month of March while its fruit ripens in October and can be picked through the first week of November.

As compared with known varieties of *Prunus persica*, the new variety is characterized by a mature leaf which is approximately one-half to one inch shorter in length, by its inflorescence which occurs approximately one month later in the season, and by the ripening of its fruit which occurs from two to three weeks later in the season.

Other distinctive characteristics of the new variety are exemplified in the accompanying illustrations.

Figure 1:
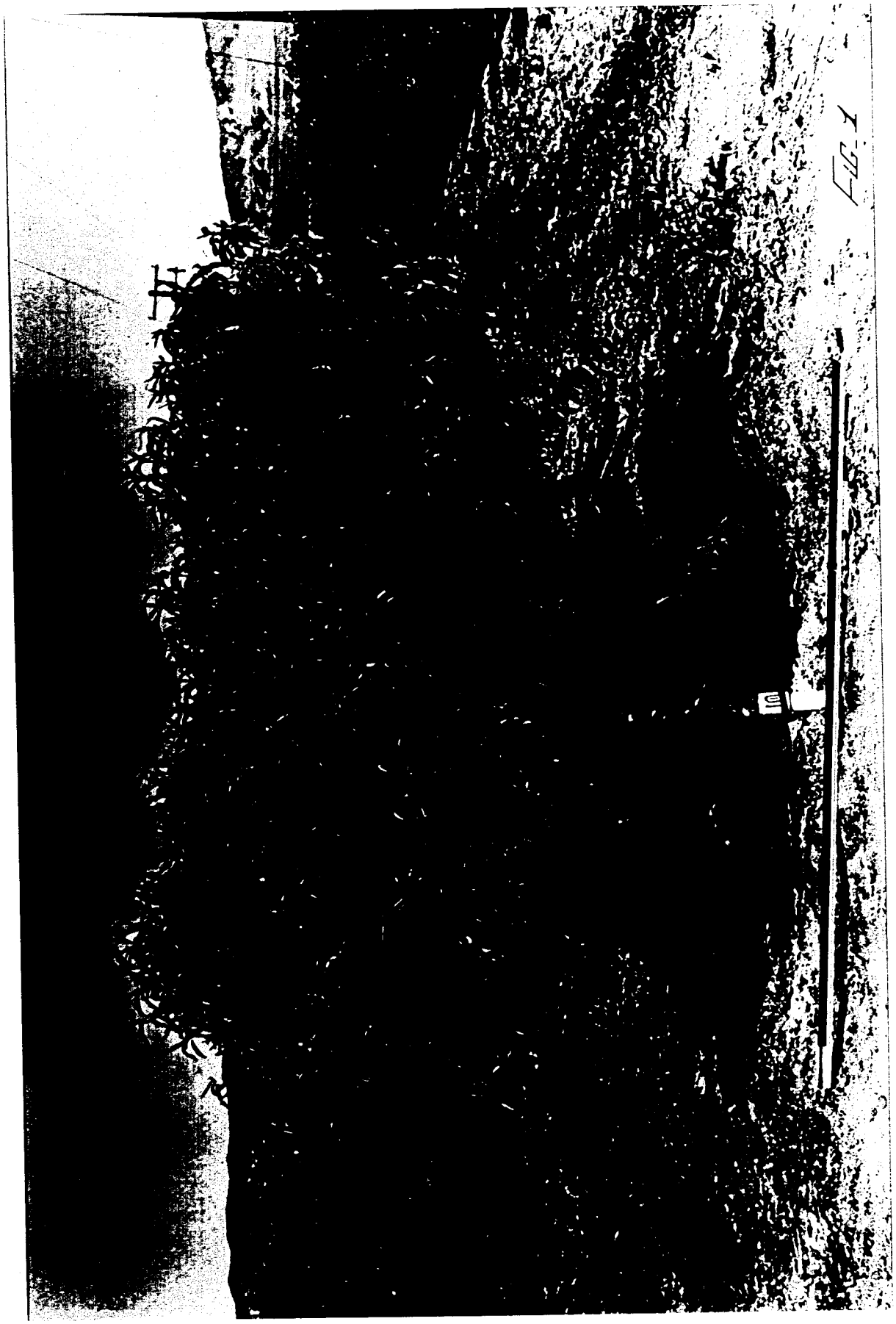
FIG. 1 shows an adult parent tree.
Figure 2:
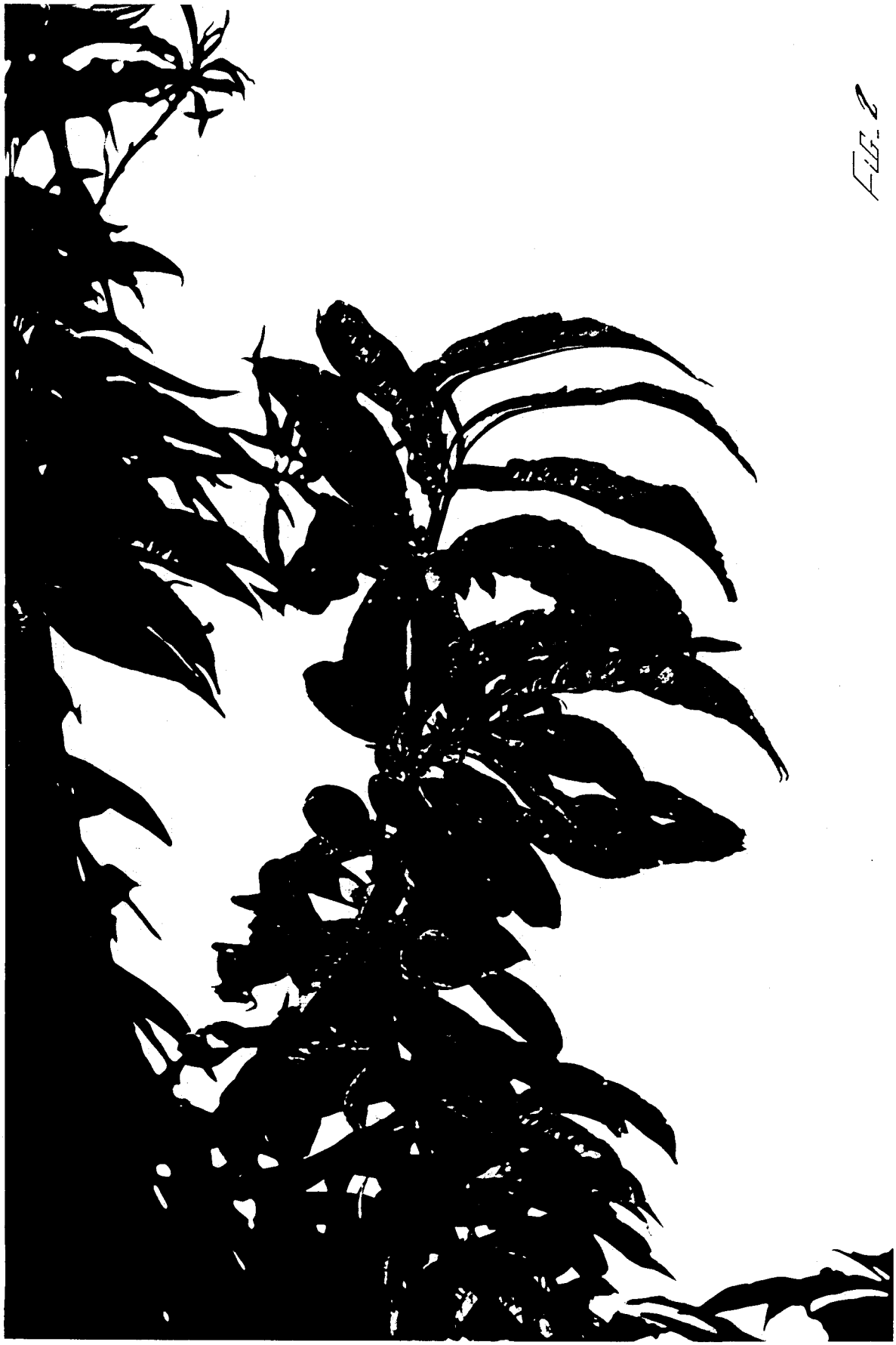
FIG. 2 is a close-up of a branch with adult leaves.
Figure 3:
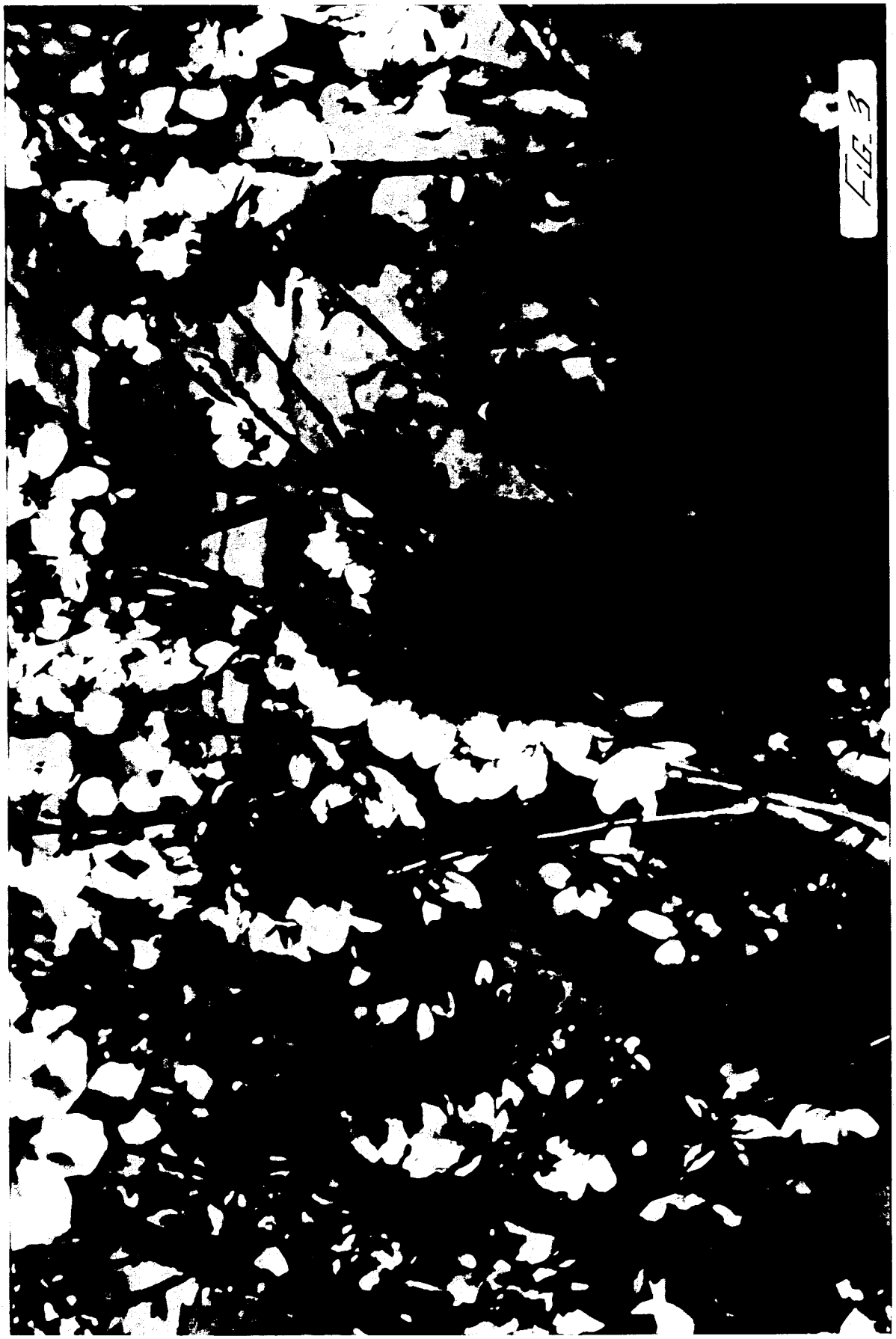
FIG. 3 is a close-up of a branch with adult inflorescence.
Figure 4:
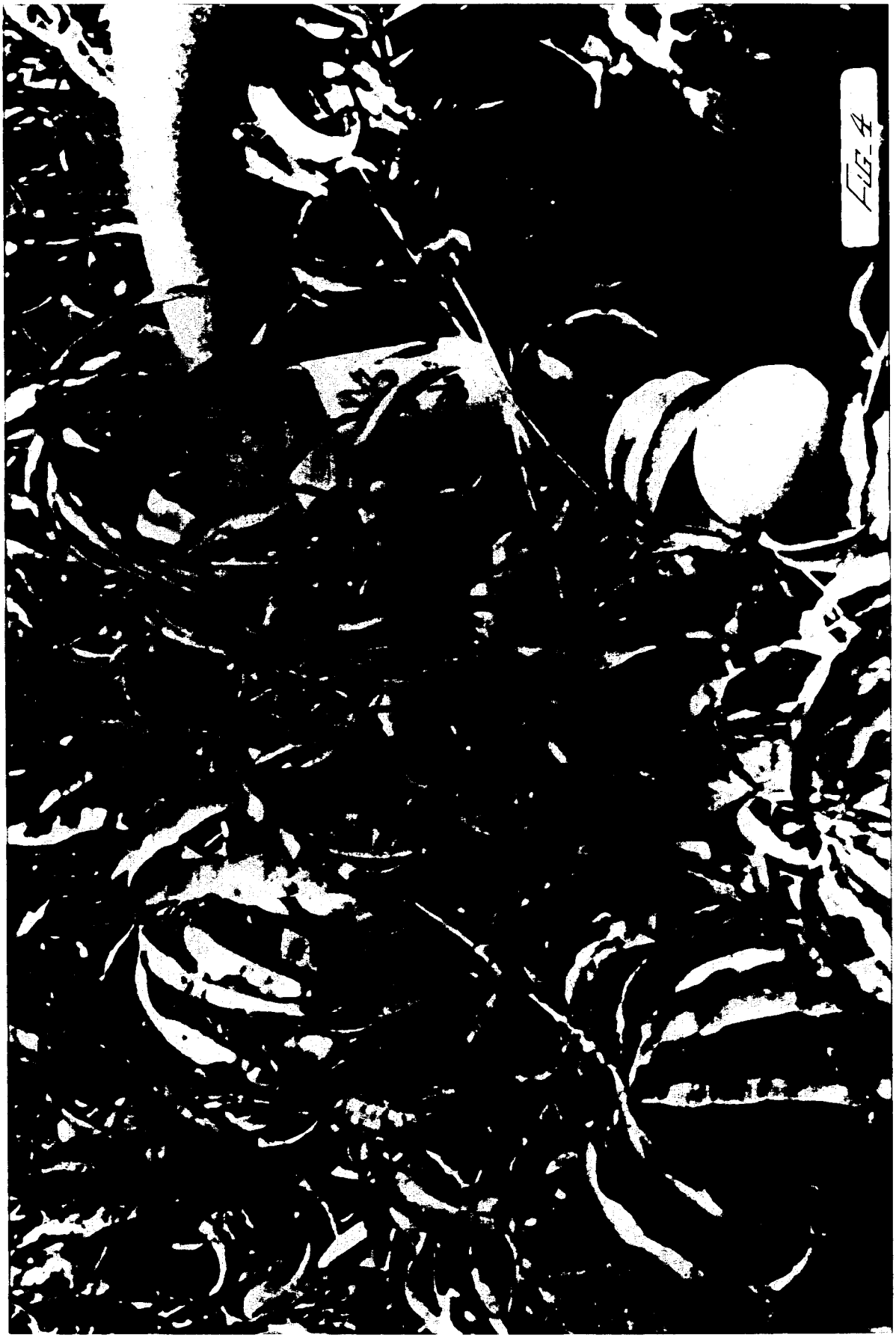
FIG. 4 is a close-up of a branch bearing ripened fruit.

The fruit color, skin and flesh, of the new variety are substantially identical to that of the Last Chance Peach variety.

TECHNICAL DESCRIPTION

The following is a description in some detail of the new variety of *Prunus persica*, Last Chance Peach Number One.

Foliage:

*Leaves.*—Obovate, spatulate, acutely pointed, medium thickness, dark green color, smooth texture, four to four and one-half inches in length and one and one-half inches in width. Glandular and finely serrate margin. Petiole of medium length and medium thickness, stipules at base. Average of eighteen glands per leaf, opposite and positioned along full length of leaf, globose to reniform, normal green color.

*Branches.*—Medium thickness, smooth texture, red to brown in color, glossy appearance, lenticels medium in number.

Flower: Pink color, inflorescent from March 1st through March 31st.

*Buds.*—Hardy, plump, medium length and somewhat appressed.

Fruit:

*Form.*—Uniform shape, shallow inconspicuous suture, circular cavity with suture showing on one side, slightly to strongly rounded ventral surface, rounded base, short apex, eight inch axial diameter and nine inch transverse diameter in suture plane.

*Skin.*—Medium thickness, not tough or tender, tenacious to flesh, abundant down that does not roll up when rubbed.

*Flesh.*—Yellow color, red color on surface of cavity, abundant amygdalin, moderate juice, firm texture, austere flavor, distinct aroma, excellent eating quality. Retains color, texture and flavor upon freezing and thawing. Fibres — fine, tender, few in number.

*Stone.*—Free, parts from flesh smoothly, short fibres, oblong to oval shape, oblique base, broad hilum, rounded apex, regularly furrowed toward apex, ridged toward apex, pitted throughout, rounded ridges, elongated pits, thick ventral edge, narrow dorsal edge, continuous ridges on either side, brownish-red color, strong tendency to split in dry season, one and one fourth inch in length and one inch in diameter.

Tree: Semi-dwarf, water frugal, vase-shaped to spherical, spreading growth, dense, medium vigor, regular bearer, very productive.

The above-described new variety of *Prunus persica* displays several novel characteristics, among them, its late fruit ripening pattern makes it a particularly desirable producer of commercial peaches during the month of October and early November for consumption as fresh fruit or preservation by canning or freezing.

What is claimed is:

1. A new and distinct variety of *Prunus persica* as described and shown herein characterized particularly by its small leaf size and its late inflorescent and fruit ripening patterns.

* * * * *